United States Patent
Heinsohn et al.

(10) Patent No.: US 7,204,974 B2
(45) Date of Patent: *Apr. 17, 2007

(54) STABILIZATION OF OXIDATION-SENSITIVE OR UV-SENSITIVE ACTIVE INGREDIENTS

(75) Inventors: Guido Heinsohn, Hamburg (DE); Anja Göppel, Hamburg (DE); Volker Wendel, Frankfurt (DE)

(73) Assignee: Beiersdorf AG, Hamburg (DE)

( * ) Notice: Subject to any disclaimer, the term of this patent is extended or adjusted under 35 U.S.C. 154(b) by 390 days.

This patent is subject to a terminal disclaimer.

(21) Appl. No.: 10/789,641

(22) Filed: Feb. 27, 2004

(65) Prior Publication Data

US 2004/0258637 A1    Dec. 23, 2004

Related U.S. Application Data

(63) Continuation of application No. PCT/EP02/09310, filed on Aug. 21, 2002.

(30) Foreign Application Priority Data

Aug. 29, 2001 (DE) ............... 101 41 475

(51) Int. Cl.
- A61K 8/00 (2006.01)
- A61K 8/04 (2006.01)
- A61K 31/53 (2006.01)
- A61Q 17/00 (2006.01)
- A61Q 17/04 (2006.01)
- A61Q 19/00 (2006.01)

(52) U.S. Cl. ............... 424/59; 424/60; 424/400; 424/401; 514/241

(58) Field of Classification Search ............... 424/59, 424/60, 400, 401; 514/241
See application file for complete search history.

(56) References Cited

U.S. PATENT DOCUMENTS

| | | | |
|---|---|---|---|
| 5,993,789 A | 11/1999 | Bonda et al. | |
| 6,113,931 A | 9/2000 | Bonda et al. | |
| 6,126,925 A | 10/2000 | Bonda et al. | |
| 6,129,909 A | 10/2000 | Bonda et al. | |
| 6,180,091 B1 | 1/2001 | Bonda et al. | |
| 6,284,916 B1 | 9/2001 | Bonda et al. | |
| 6,355,230 B2 * | 3/2002 | Gers-Barlag et al. | 424/59 |
| 6,355,261 B1 | 3/2002 | Bonda et al. | |
| 6,368,578 B1 * | 4/2002 | Gers-Barlag et al. | 424/59 |
| 6,403,067 B1 | 6/2002 | Schamper et al. | |
| 6,440,402 B1 * | 8/2002 | Gonzalez et al. | 424/59 |
| 6,468,511 B1 | 10/2002 | Chopra et al. | |
| 6,491,901 B2 * | 12/2002 | Gers-Barlag et al. | 424/59 |
| 2001/0022966 A1 | 9/2001 | Gers-Barlag et al. | |
| 2001/0026790 A1 | 10/2001 | Gers-Barlag et al. | |
| 2002/0164296 A1 | 11/2002 | Schamper et al. | |
| 2002/0192172 A1 | 12/2002 | Chopra et al. | |
| 2003/0170284 A1 | 9/2003 | Dorschner et al. | |

FOREIGN PATENT DOCUMENTS

| | | |
|---|---|---|
| DE | 199 49 825 A1 | 4/2001 |
| FR | 2 801 206 A | 5/2001 |
| FR | 2 801 207 A | 5/2001 |
| FR | 2 801 208 A | 5/2001 |
| FR | 2 801 209 A | 5/2001 |
| FR | 2 801 210 A1 | 5/2001 |
| FR | 2 801 213 A1 | 5/2001 |
| GB | 660131 A | 10/1951 |
| WO | WO 02 17873 A | 3/2002 |

OTHER PUBLICATIONS

"Illinois Researcher Receives Award for Developing a Better Sunscreen," EurekAlert! released Jun. 7, 2001 (http://www.eurekalert.org).

"Beauty is Skin Deep," Household and Personal Products Industry (HAPPI), posted online Sep. 2000 (http://www.happi.com/special/sep002.htm).

International Search Report from corresponding International Application No. PCT/EP02/08577, dated Dec. 20, 2002.

German Search Report dated Mar. 27, 2002 for German Application No. DE 101 41 472.2.

German Search Report dated Apr. 12, 2002 for German Application No. DE 101 41 473.0.

Bonda C Et Al: "A New Photostabilizer For Full Spectrum Sunscreens" Cosmetics & Toiletries, Wheaton, IL, US, vol. 115, No. 6, 2000, pp. 37-45.

(Continued)

Primary Examiner—Shelley A. Dodson
(74) Attorney, Agent, or Firm—Greenblum & Bernstein, P.L.C.

(57) ABSTRACT

The invention is a cosmetic or dermatological formulation, comprising:
(a) at least one oxidation- and/or UV-sensitive active ingredient;
(b) at least one dialkyl naphthalate which is characterized by the structural formula

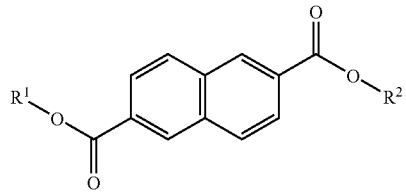

in which $R^1$ and $R^2$, independently of one another, are chosen from the group of branched and unbranched alkyl groups having 6 to 24 carbon atoms; and
(c) at least one lipid with a polarity of at most 30 mN/m. The present invention also includes method of using the cosmetic or dermatological formulations.

25 Claims, No Drawings

OTHER PUBLICATIONS

International Search Report from corresponding International Application No. PCT/EP02/09309 dated Sep. 30, 2003.
International Search Report from corresponding International Application No. PCT/EP02/09374 dated Sep. 30, 2003.
International Search Report from corresponding International Application No. PCT/EP02/09375 dated Dec. 10, 2002.
International Search Report from corresponding International Application No. PCT/EP02/09567, dated Sep. 30, 2003.
International Search Report from corresponding International Application No. PCT/EP02/09543 dated Oct. 2, 2003.
International Search Report from corresponding International Application No. PCT/EP02/009310 dated Apr. 12, 2002.
German Search Report for 101 41 474.9 dated Apr. 15, 2002.
German Search Report for 101 41 478.1 dated Apr. 15, 2002.
German Search Report for 101 41 475.7 dated Jul. 19, 2002.

* cited by examiner

STABILIZATION OF OXIDATION-SENSITIVE OR UV-SENSITIVE ACTIVE INGREDIENTS

CROSS-REFERENCE TO RELATED APPLICATIONS

This is a continuation application of PCT/EP02/09310, filed Aug. 21, 2002, which is incorporated herein by reference in its entirety, and also claims the benefit of German Priority Application No. 101 41 475.7, filed Aug. 29, 2001.

FIELD OF THE INVENTION

The present invention relates to substance combinations for stabilizing oxidation-sensitive and/or UV-sensitive active ingredients, and to cosmetic and dermatological formulations with oxidation-sensitive and/or UV-sensitive active ingredients stabilized in this way. In particular, it relates to cosmetic and dermatological photoprotective formulations and formulations with UV-sensitive photoprotective filter substances which are stabilized through the use of these substance combinations.

BACKGROUND OF THE INVENTION

The harmful effects of the ultraviolet part of solar radiation on the skin are generally known. The rays have different effects on the skin organ depending on their particular wavelength: so-called UV-C radiation with a wavelength below 290 nm is absorbed by the ozone layer in the earth's atmosphere and therefore is of no physiological importance. By contrast, rays in the range between 290 nm and 320 nm, the so-called UV-B region, cause erythema, simple sunburn or even burns of greater or lesser severity. A maximum for the erythema activity of sunlight is stated as being the relatively narrow range around 308 nm.

Numerous compounds are known for protecting against UV-B radiation, examples thereof being derivatives of 3-benzylidenecamphor, of 4-aminobenzoic acid, of cinnamic acid, of salicylic acid, of benzophenone, and of triazine.

It has long been incorrectly assumed that the long-wave UV-A radiation with a wavelength between 320 nm and 400 nm has only a negligible biological effect. However, it has now been proven by numerous studies that UV-A radiation is far more hazardous than UV-B radiation with regard to the triggering of photodynamic, specifically phototoxic, reactions and chronic changes in the skin. The harmful effect of UV-B radiation can also be further intensified by UV-A radiation.

Thus, it has been proven, inter alia, that even UV-A radiation under entirely normal everyday conditions is sufficient to damage within a short time the collagen and elastin fibers which are of essential importance for the structure and firmness of the skin. This results in chronic photoinduced changes in the skin—the skin "ages" prematurely. The clinical appearance of skin aged by light includes, for example, wrinkles and lines and an irregular, furrowed relief. In addition, the areas affected by photoinduced skin aging may have irregular pigmentation. The formation of brown spots, keratoses and even carcinomas or malignant melanomas is also possible. Skin aged prematurely by everyday exposure to UV is additionally characterized by a lower activity of the Langerhans cells and a slight chronic inflammation.

Approximately 90% of the ultraviolet radiation which reaches the earth consists of UV-A rays. Whereas UV-B radiation varies greatly depending on numerous factors (for example time of year and time of day or latitude), UV-A radiation remains relatively constant from day to day irrespective of seasonal and diurnal or geographic factors. At the same time, most of the UV-A radiation penetrates into the living epidermis, while about 70% of the UV-B rays are retained by the horny layer.

It is therefore of fundamental importance that cosmetic and dermatological photoprotective preparations provide adequate protection both against UV-B and against UV-A radiation.

In general, the light absorption behavior of photoprotective filter substances is very well known and documented, especially since most industrialized countries have positive lists for the use of such substances, which impose very strict standards on the documentation.

However, the concentration in which known photoprotective filter substances present as solids are used is often restricted—in particular in combination with other substances which are to be dissolved. There are thus certain technical difficulties with regard to formulating in achieving relatively high sun protection factors and UV-A protection performance.

Advantageous UV-A filter substances are e.g. dibenzoylmethane derivatives, in particular 4-(tert-butyl)-4'-methoxydibenzoylmethane (CAS No. 70356-09-1), which is sold by Givaudan under the name Parsol® 1789 and by Merck under the trade name Eusolex® 9020.

The main disadvantage of all dibenzoylmethane derivatives which absorb in the UV region is a certain instability toward UV radiation, meaning that these components are decomposed under the influence of UV to give inactive products and are no longer available for UV absorption. Preparations of the prior art with a content of these substances therefore expediently also comprise certain UV stabilizers such as, for example, ethylhexyl 2-cyano-3,3-diphenylacrylate (octocrylene) or 4-methylbenzylidene-camphor.

SUMMARY OF THE INVENTION

An object of the present invention was to overcome the disadvantages of the prior art and to arrive in a simple manner at preparations which are distinguished by a high UV, in particular UV-A, protection performance and in which the use of customary UV stabilizers can be dispensed with.

The prior art also recognizes a series of different efficient, lipophilic skincare active ingredients—such as, for example, ubiquinones, retinoids and carotenoids—which contain unsaturated, aromatic or benzoidal structural elements, the use of which in cosmetic or dermatological formulations, in particular in formulations of the oil-in-water type, is very desirable. Unfortunately, however, substances of this kind are often very unstable meaning that, particularly if exposed to UV radiation, they rapidly decompose and thereby lose their effectiveness.

It was therefore a further object of the present invention to increase the stability of oxidation-sensitive and/or UV-sensitive active ingredients, and to provide stable preparations with oxidation-sensitive and/or UV-sensitive active ingredients whose effectiveness is retained over a long period.

It was surprising and could not have been foreseen by the person skilled in the art that cosmetic and dermatological formulations containing at least one oxidation- and/or UV-sensitive active ingredient, which comprise
  (a) at least one dialkyl naphthalate which is distinguished by the structural formula

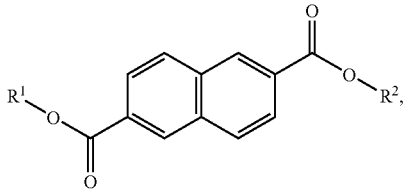

in which $R^1$ and $R^2$, independently of one another, are chosen from the group of branched and unbranched alkyl groups having 6 to 24 carbon atoms, and
  (b) at least one lipid with a polarity of at most 30 mN/m overcome the disadvantages of the prior art.

If the oxidation- and/or UV-sensitive active ingredient(s) are present in a formulation according to the invention, then they are protected in an excellent manner against the decomposition induced by UV radiation. This is true in particular for dibenzoylmethane derivatives.

The invention therefore also provides for the use of substance combinations which comprise
  (a) at least one dialkyl naphthalate which is characterized by the structural formula

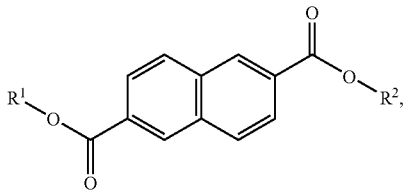

in which $R^1$ and $R^2$, independently of one another, are chosen from the group of branched and unbranched alkyl groups having 6 to 24 carbon atoms, and
  (b) at least one lipid with a polarity of at most 30 mN/m for stabilizing cosmetic or dermatological active ingredients against decomposition induced by UV radiation.

DETAILED DESCRIPTION OF THE PREFERRED EMBODIMENTS

As well as one or more oil phases, the preparations within the meaning of the present invention may preferably additionally comprise one or more water phases and be present, for example, in the form of W/O, O/W, W/O/W or O/W/O emulsions. Such formulations may preferably also be a microemulsion, a PIT emulsion, a solids emulsions (i.e. an emulsion which is stabilized by solids, e.g. a Pickering emulsion), a sprayable emulsion or a hydrodispersion.

The preparations according to the invention are entirely satisfactory preparations in every respect which are not restricted to the limited choice of raw materials. Accordingly, they are very particularly suitable for use as bases for preparation forms with diverse application purposes. The preparations according to the invention exhibit very good sensory and cosmetic properties, such as, for example, extensibility on the skin or the ability to absorb into the skin, and are further distinguished by very good photoprotection effectiveness coupled with excellent skincare data.

It was particularly surprising that with the use according to the present invention it is possible to dispense entirely with the use of further UV stabilizers, in particular with the use of ethylhexyl 2-cyano-3,3-diphenylacrylate (octocrylene) or 4-methylbenzylidenecamphor.

In addition, the use according to the invention surprisingly allows the stability of lipophilic active ingredients in cosmetic or dermatological formulations (O/W formulations) to be considerably increased compared with the prior art.

The invention thus also provides for the use of substance combinations which comprise
  (a) at least one dialkyl naphthalate which is characterized by the structural formula

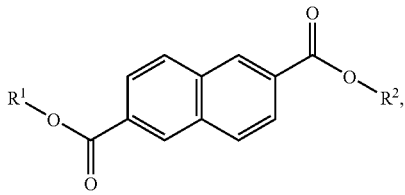

in which $R^1$ and $R^2$, independently of one another, are chosen from the group of branched and unbranched alkyl groups having 6 to 24 carbon atoms, and
  (b) at least one lipid with a polarity of at most 30 mN/m for improving the effectiveness and increasing the stability of lipophilic active ingredients in cosmetic or dermatological preparations.

Advantageous lipophilic active ingredients which are stabilized in an excellent manner by the use according to the invention are those whose log P value is greater than 3.5. P is the partition coefficient, which is defined as the ratio of the equilibrium concentration of a dissolved substance in a two-phase system which consists of two solvents which are essentially immiscible with one another. These two solvents are, in the present case, n-octanol and water, i.e.

$$P_{ow} = \frac{c_{n\text{-}octanol}}{c_{water}}$$

It is advantageous for the purposes of the present invention to choose the lipophilic active ingredient(s) from the group of ubiquinones and plastoquinones. For the purposes of the present invention, coenzyme Q10, which has a log P value of about 15, is very particularly advantageous.

Further lipophilic active ingredients which are advantageous according to the invention are retinoids (vitamin A acid and/or derivatives thereof) or vitamin A and/or derivatives thereof. The group of retinoids advantageous according to the invention is defined as including all cosmetically and/or pharmaceutically acceptable retinoids, including retinol and its esters, retinal and also retinoic acid (vitamin A acid) and esters thereof. For the purposes of the present invention, retinol (with a log P value of about 7) and retinyl palmitate (with a log P value of about 13) are particularly advantageous.

Further lipophilic acid ingredients advantageous according to the invention are carotenoids. For the purposes of the present invention, β-carotene, which has a log P value of 15, for example, is particularly advantageous.

Further lipophilic active ingredients advantageous according to the invention are:
lipoic acid and derivatives,
vitamin E and derivatives,
vitamin F,
dioic acid [8-hexadecene-1,16-dicarboxylic acid (CAS number 20701-68-2)]

The amount of lipophilic active ingredients (one or more compounds) in the preparations is preferably 0.0001 to 10% by weight, particularly preferably 0.001 to 5% by weight, based on the total weight of the preparation.

Advantageous for the purposes of the present invention are dialkyl naphthalates in which $R^1$ and/or $R^2$ are branched alkyl groups having 6 to 10 carbon atoms. Very particular preference for the purposes of the present invention is given to diethylhexyl naphthalate, which is obtainable, for example, under the trade name Hallbrite TQ™ from CP Hall or Corapan TQ™ from H&R.

According to the invention, cosmetic or dermatological preparations advantageously comprise 0.001 to 30% by weight, preferably 0.01 to 20% by weight, very particularly preferably 0.5 to 15% by weight, of one or more dialkyl naphthalates.

The oil phase(s) of the preparations according to the invention is/are advantageously chosen from the group of polar lipids with a polarity of ≦30 mN/m. The lipid or lipids according to the invention are particularly advantageously chosen from the group of lipids with a polarity of from 5 to 25 mN/m.

Particularly advantageous lipids for the purposes of the present invention are all native lipids, such as e.g. olive oil, sunflower oil, soybean oil, groundnut oil, rapeseed oil, almond oil, palm oil, coconut oil, castor oil, wheatgerm oil, grapeseed oil, thistle oil, evening primrose oil, macadamia nut oil, corn oil, avocado oil, and the like, and those listed below.

| Manufacturer | Trade name | INCI name | Polarity mN/m |
|---|---|---|---|
| Stearinerie Dubois Fils | DUB VCI 10 | Isodecyl Neopentanoate | 29.9 |
| ALZO (ROVI) | Dermol IHD | Isohexyl Decanoate | 29.7 |
| ALZO (ROVI) | Dermol 108 | Isodecyl Octanoate | 29.6 |
| | Dihexyl ether | Dihexyl Ether | 29.2 |
| ALZO (ROVI) | Dermol 109 | Isodecyl 3,5,5-Trimethyl Hexanoate | 29.1 |
| Henkel Cognis | Cetiol SN | Cetearyl Isononanoate | 28.6 |
| Unichema | Isopropyl palmitate | Isopropyl Palmitate | 28.8 |
| Dow Corning | DC Fluid 345 | Cyclomethicone | 28.5 |
| Dow Corning | Dow Corning Fluid 244 | Cyclopolydimethylsiloxane | 28.5 |
| Nikko Chemicals Superior Jojoba Oil Gold | Jojoba oil gold | | 26.2 |
| Wacker | Wacker AK 100 | Dimethicone | 26.9 |
| ALZO (ROVI) | Dermol 98 | 2-Ethylhexanoic acid 3,5,5-trimethyl ester | 26.2 |
| Dow Corning | Dow Corning Fluid 246 | Offen | 25.3 |
| Henkel Cognis | Eutanol G | Octyldodecanol | 24.8 |
| Condea Chemie | Isofol 16 | Hexyl Decanol | 24.3 |
| ALZO (ROVI) | Dermol 139 | Isotridecyl 3,5,5-trimethylhexanonanoate | 24.5 |
| Henkel Cognis | Cetiol PGL | Hexyldecanol (+) Hexyl Decyl Laurate | 24.3 |
| | Cegesoft C24 | Octyl Palmitate | 23.1 |
| Gattefossé | M.O.D. | Octyldodecyl Myristate | 22.1 |
| | Macadamia Nut Oil | | 22.1 |
| Bayer AG, Dow Corning | Silicone oil VP 1120 | Phenyl Trimethicone | 22.7 |
| CONDEA Chemie | Isocarb 12 | Butyl Octanoic Acid | 22.1 |
| Henkel Cognis | Isopropyl stearate | Isopropyl Stearate | 21.9 |
| WITCO, Goldschmidt | Finsolv TN | C12–15 Alkyl Benzoate | 21.8 |
| Dr. Straetmans | Dermofeel BGC | Butylene Glycol Caprylate/Caprate | 21.5 |
| Unichema Huels | Miglyol 812 | Caprylic/Capric Triglyceride | 21.3 |
| Trivent (via S. Black) | Trivent OCG | Tricaprylin | 20.2 |
| ALZO (ROVI) | Dermol 866 | PEG diethyl hexanoate/diisononanoate/ethylhexyl isononanoate | 20.1 |
| Condea Chemie | Isofol 14 T | Butyl Decanol (+) Hexyl Octanol (+) Hexyl Decanol (+) Butyl Octanol | 19.8 |
| Lipochemicals INC./USA (Induchem) | Lipovol MOS-130 | Tridecyl Stearate (+) Tridecyl Trimellitate (+) Dipentaerythrityl Hexacaprylate/hexacaprate | 19.4 |
| | Castor oil | | 19.2 |
| CONDEA Chemie | Isofol ester 0604 | | 19.1 |

| Manufacturer | Trade name | INCI name | Polarity mN/m |
|---|---|---|---|
| Huels CONDEA Chemie | Miglyol 840 | Propylene Glycol Dicaprylate/Dicaprate | 18.7 |
| CONDEA Chemie | Isofol 12 | Butyl Octanol | 17.4 |
| Goldschmidt | Tegosoft SH | Stearyl Heptanoate | 17.8 |
| | Avocado oil | | 14.5 |
| Henkel Cognis | Cetiol B | Dibutyl Adipate | 14.3 |
| ALZO (ROVI) | Dermol 488 | PEG 2 Diethylene Hexanoate | 10.1 |
| Condea Augusta S.P.A. | Cosmacol ELI | C12–13 Alkyl Lactate | 8.8 |
| ALZO (ROVI) | Dermol 489 | Diethylene Glycol Dioctanoate/Diisononanoate | 8.6 |
| Condea Augusta S.P.A. | Cosmacol ETI | Di-C12–13 Alkyl Tartrate | 7.1 |
| Henkel Cognis | Emerest 2384 | Propylene Glycol Monoisostearate | 6.2 |
| Henkel Cognis | Myritol 331 | Cocoglycerides | 5.1 |
| Unichema | Prisorine 2041 GTIS | Triisostearin | 2.4 |

Of the hydrocarbons, paraffin oil, and further hydrogenated polyolefins, such as hydrogenated polyisobutenes, squalane and squalene, in particular, are to be used advantageously for the purposes of the present invention.

Further advantageous lipids according to the invention with a polarity of at most 30 mN/m are UV filter substances which are liquid at room temperature, in particular homomenthyl salicylate (INCI: homosalate), 2-ethylhexyl 2-cyano-3,3-diphenylacrylate (INCI: Octocrylene), 2-ethylhexyl 2-hydroxybenzoate (2-ethylhexyl salicylate, octyl salicylate, INCI: Octyl Salicylate) and esters of cinnamic acid, preferably 4-methoxy-cinnamic 2-ethylhexyl ester (2-ethylhexyl 4-methoxycinnamate, INCI: Octyl Methoxy-cinnamate) and 4-methoxycinnamic isopentyl ester (isopentyl 4-methoxycinnamate, INCI: Isoamyl p-methoxycinnamate).

In addition, the preparations according to the invention can accordingly also advantageously be in the form of so-called oil-free cosmetic or dermatological emulsions, which comprise a water phase and at least one UV filter substance which is liquid at room temperature and/or one or more silicone derivatives as further phase. Oil-free formulations for the purposes of the present invention may advantageously also comprise further lipophilic components—such as, for example, lipophilic active ingredients.

It is in some instances also advantageous, although not obligatory, if the lipid phase comprises up to 50% by weight, based on the total weight of the lipid phase, of lipids with a polarity of ≧30 mN/m and/or cyclic or linear silicone oils and/or silicone waxes.

Advantageous further lipids for the purposes of the present invention are, for example, those listed below:

| INCI Name | Polarity mN/m |
|---|---|
| Cycloparaffin | 49.1 |
| Polydecene | 46.7 |
| Hydrogenated Polyisobutene | 44.7 |
| Polydimethylsiloxane | 46.5 |
| Isohexadecane | 43.8 |
| Mineral Oil | 43.7 |
| Mineral Oil | 43.7 |
| Polydimethylsiloxane | 42.4 |
| Isoeicosane | 41.9 |
| Polydimethylsiloxane | 40.9 |
| Ethoxydiglycol Oleate | 40.5 |
| Decyl Olivate | 40.3 |
| Dioctylcyclohexane | 39.0 |
| Mineral Oil | 38.3 |
| Paraffinum Liquidum | 37.6 |
| Isocetyl Palmitate | 36.2 |
| Cyclopentasiloxane | 32.3 |
| Octyl Isostearate | 31.6 |
| Dicaprylyl Carbonate | 31.7 |
| Trimethylhexyl Isononanoate | 31.1 |
| 2-Ethylhexyl Isononanoate | 31.0 |
| Octyl Cocoate | 30.0 |

The oil phase can advantageously also have a content of cyclic or linear silicone oils or consist entirely of such oils, although it is preferred to use an additional content of other oil phase components apart from the silicone oil or the silicone oils.

Silicone oils are high molecular weight synthetic polymeric compounds in which silicon atoms are linked in a chain-like and/or network-like manner via oxygen atoms, and the remaining valences of the silicon are saturated by hydrocarbon radicals (in most cases methyl, less often ethyl, propyl, phenyl groups etc.). Systematically, the silicone oils are referred to as polyorganosiloxanes. The methyl-substituted polyorganosiloxanes which represent the most significant compounds of this group in terms of number are characterized by the following structural formula

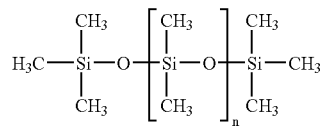

are also referred to as polydimethylsiloxane or Dimethicone (INCI). There are dimethicones with various chain lengths and with various molecular weights.

For the purposes of the present invention, particularly advantageous polyorganosiloxanes are, for example, dimethylpolysiloxanes [poly(dimethylsiloxane)], which are available, for example, under the trade names Abil 10 to 10 000 from Th. Goldschmidt. Also advantageous are phenylmethylpolysiloxanes (INCI: Phenyl Dimethicone, Phenyl Trimethicone), cyclic silicones (octamethylcyclotetrasiloxane or decamethylcyclopentasiloxane), which are also referred to as Cyclomethicones in accordance with INCI, amino-modified silicones (INCI: Amodimethicone) and silicone waxes, e.g. polysiloxane-polyalkylene copolymers (INCI: Stearyl Dimethicone and Cetyl Dimethicone) and dialkoxydimethylpolysiloxanes (Stearoxy Dimethicone and Behenoxy Stearyl Dimethicone), which are available as various Abil wax grades from Th. Goldschmidt. Other silicone oils can, however, also be used advantageously for the purposes of the present invention, for example cetyldimethicone, hexamethylcyclotrisiloxane, polydimethylsiloxane, poly(methylphenylsiloxane).

The cosmetic or dermatological photoprotection formulations according to the invention can have the customary composition and be used for cosmetic or dermatological photoprotection, in addition for the treatment, care and cleansing of the skin and/or of the hair and as a make-up product in decorative cosmetics.

Depending on their formulation, cosmetic or topical dermatological compositions for the purposes of the present invention may be used, for example, as skin protection cream, cleansing milk, day or night cream etc. It is in some cases possible and advantageous to use the compositions according to the invention as a basis for pharmaceutical formulations.

For use, the cosmetic and dermatological preparations are applied to the skin and/or the hair in a sufficient amount in the manner customary for cosmetics.

The cosmetic and dermatological preparations according to the invention can comprise cosmetic auxiliaries as are customarily used in such preparations, e.g. preservatives, preservation helpers, bactericides, perfumes, substances to prevent foaming, dyes, pigments which have a coloring action, thickeners, moisturizing and/or humectant substances, fillers which improve the feel of the skin, fats, oils, waxes or other customary constituents of a cosmetic or dermatological formulation, such as alcohols, polyols, polymers, foam stabilizers, electrolytes, organic solvents or silicone derivatives.

Advantageous preservatives for the purposes of the present invention are, for example, formaldehyde donors (such as e.g. DMDM hydantoin, which is available, for example, under the trade name Glydant™ from Lonza), iodopropyl butylcarbamates (e.g. those available under the trade names Glycacil-L, Glycacil-S from Lonza, and/or Dekaben LMB from Jan Dekker), parabens (i.e. p-hydroxybenzoic-alkyl esters, such as methyl, ethyl-, propyl- and/or butylparaben), phenoxyethanol, ethanol, benzoic acid and the like. According to the invention, the preservative system usually also advantageously includes preservation helpers, such as, for example, octoxyglycerol, glycine soya etc. as well.

Particularly advantageous preparations are also obtained when antioxidants are used as additives or active ingredients. According to the invention, the preparations advantageously comprise one or more antioxidants. Favorable, but nevertheless optional antioxidants which may be used are all antioxidants customary or suitable for cosmetic and/or dermatological applications.

For the purposes of the present invention, it may be particularly advantageous to use water-soluble antioxidants, such as, for example, vitamins, e.g. ascorbic acid and derivatives thereof, and D-biotin, natural and/or synthetic isoflavonoids, alpha-glucosylrutin, panthenol, aloe vera.

The amount of antioxidants (one or more compounds) in the preparations is preferably 0.001 to 30% by weight, particularly preferably 0.05 to 20% by weight, in particular 0.1 to 10% by weight, based on the total weight of the preparation.

It is particularly advantageous when the cosmetic preparations according to the present invention comprise cosmetic or dermatological active ingredients, preferred active ingredients being antioxidants which can protect the skin against oxidative stress.

Advantageous further active ingredients are natural active ingredients and/or derivatives thereof, such as e.g. phytoene, carnitine, carnosine, creatine, taurine and/or β-alanine.

Formulations according to the invention, which comprise e.g. known antiwrinkle active ingredients, such as flavone glycosides (in particular α-glycosylrutin), coenzyme Q10, vitamin E and/or derivatives and the like, are particularly advantageously suitable for the prophylaxis and treatment of cosmetic or dermatological changes in skin, as arise, for example, during skin aging (such as, for example, dryness, roughness and formation of dryness wrinkles, itching, reduced refatting (e.g. after washing), visible vascular dilations (teleangiectases, couperosis), flaccidity and formation of wrinkles and lines, local hyperpigmentation, hypopigmentation and abnormal pigmentation (e.g. age spots), increased susceptibility to mechanical stress (e.g. cracking) and the like). In addition, they are advantageously suitable against the appearance of dry or rough skin.

The water phase of the preparations according to the invention can advantageously comprise customary cosmetic auxiliaries, such as, for example, alcohols, in particular those of low carbon number, preferably ethanol and/or isopropanol, diols or polyols of low carbon number, and ethers thereof, preferably propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, polymers, foam stabilizers, electrolytes, and in particular one or more thickeners which may advantageously be chosen from the group consisting of silicon dioxide, aluminum silicates, polysaccharides or derivatives thereof, e.g. hyaluronic acid, xanthan gum, hydroxypropylmethylcellulose, particularly advantageously from the group of polyacrylates, preferably a polyacrylate from the group of so-called carbopols, for example Carbopol 980, 981, 1382, 2984, 5984, in each case individually or in combination. Moisturizers can also preferably be used.

Also advantageous are copolymers of $C_{10\text{-}30}$-alkyl acrylates and one or more monomers of acrylic acid, of methacrylic acid or esters thereof which are crosslinked with an allyl ether of sucrose or an allyl ether of pentaerythritol.

Compounds which bear the INCI name "Acrylates/$C_{10\text{-}30}$ Alkyl Acrylate Crosspolymer" are advantageous. Those availabe under the trade names Pemulen TR1 and Pemulen TR2 from B. F. Goodrich Company are particularly advantageous.

Compounds which bear the INCI name Ammonium Acryloyldimethyltaurate/Vinylpyrrolidone copolymers are advantageous.

According to the invention, the Ammonium Acryloyldimethyltaurate-/Vinylpyrrolidone copolymers advantageously have the empirical formula $[C_7H_{16}N_2SO_4]n$ $[C_6H_9NO]_m$, corresponding to a statistical structure as follows

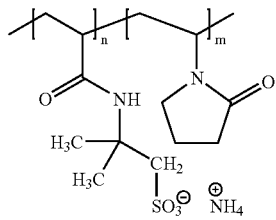

Preferred species for the purposes of the present invention are listed in Chemical Abstracts under the Registry numbers 58374-69-9, 13162-05-5 and 88-12-0 and are available under the trade name Aristoflex® AVC from Clariant GmbH.

Also advantageous are copolymers/crosspolymers comprising Acryloyldimethyl Taurate, such as, for example, Simugel® EG or Simugel® EG from Seppic S.A.

Moisturizers is the term used for substances or mixtures of substances which, following application or distribution on the surface of the skin, confer on cosmetic or dermatological preparations the property of reducing the moisture loss by the horny layer (also called transepidermal water loss (TEWL)) and/or have a positive influence on the hydration of the horny layer.

Advantageous moisturizers for the purposes of the present invention are, for example, glycerol, lactic acid and/or lactates, in particular sodium lactate, butylene glycol, propylene glycol, biosaccharide gum-1, glycine soya, ethylhexyloxyglycerol, pyrrolidonecarboxylic acid and urea. In addition, it is particularly advantageous to use polymeric moisturizers from the group of water-soluble and/or water-swellable and/or water-gellable polysaccharides. Particularly advantageous are, for example, hyaluronic acid, chitosan and/or a fucose rich polysaccharide which is listed in Chemical Abstracts under the Registry number 178463-23-5 and is available, for example, under the name Fucogel®1000 from SOLABIA S.A.

The cosmetic or dermatological preparations according to the invention can also advantageously, but not necessarily, comprise fillers which, for example, further improve the sensory and cosmetic properties of the formulations and, for example, bring about or intensify a velvety or silky feel on the skin. Advantageous fillers for the purposes of the present invention are starch and starch derivatives (such as tapioca starch, distarch phosphate, aluminum or sodium starch octenylsuccinate and the like), pigments which primarily have neither a UV filter effect nor a coloring effect (such as e.g. boron nitride etc.) and/or Aerosils® (CAS No. 7631-86-9).

For the purposes of the present invention, it is also advantageous to create cosmetic and dermatological preparations whose main purpose is not protection against sunlight, but which nevertheless contain a content of further UV protection substances. Thus, for example, UV-A and/or UV-B filter substances are usually incorporated into day creams or make-up products. UV protection substances, like antioxidants and, if desired, preservatives, also represent effective protection of the preparations themselves against decay. Also favorable are cosmetic and dermatological preparations which are in the form of a sunscreen composition.

Accordingly, the preparations within the meaning of the present invention preferably comprise at least one further UV-A, UV-B and/or broadband filter substance. The formulations may, but do not necessarily, optionally also comprise one or more organic and/or inorganic pigments as UV filter substances, which may be present in the water phase and/or the oil phase.

Preferred inorganic pigments are metal oxides and/or other metal compounds which are sparingly soluble or insoluble in water, in particular oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides, and the sulfate of barium ($BaSO_4$).

The pigments can advantageously be used for the purposes of the present invention also in the form of commercially available oily or aqueous predispersions. Dispersion auxiliaries and/or solubility promoters may advantageously be added to these predispersions.

The pigments may, according to the invention, advantageously be surface-treated ("coated"), the intention being, for example, to form or retain a hydrophilic, amphiphilic or hydrophobic character. This surface treatment can consist in providing the pigments with a thin hydrophilic and/or hydrophobic inorganic and/or organic layer by methods known per se. The various surface coatings for the purposes of the present invention may also comprise water.

Inorganic surface coatings for the purposes of the present invention may consist of aluminum oxide ($Al_2O_3$), aluminum hydroxide $Al(OH)_3$, or aluminum oxide hydrate (also: alumina, CAS No.: 1333-84-2), sodium hexametaphosphate $(NaPO_3)_6$, sodium metaphosphate $(NaPO_3)_n$, silicon dioxide ($SiO_2$) (also: silica, CAS No.: 7631-86-9), or iron oxide ($Fe_2O_3$). These inorganic surface coatings may exist on their own, in combination and/or in combination with organic coating materials.

Organic surface coatings for the purposes of the present invention may consist of vegetable or animal aluminum stearate, vegetable or animal stearic acid, lauric acid, dimethylpolysiloxane, (also: dimethicone), methylpolysiloxane (methicone), simethicone (a mixture of dimethylpolysiloxane with an average chain length of from 200 to 350 dimethylsiloxane units and silicagel) or alginic acid. These organic surface coatings may exist on their own, in combination and/or in combination with inorganic coating materials.

Zinc oxide particles and predispersions of zinc oxide particles which are suitable according to the invention are available under the following trade names from the companies listed:

| Trade name | Coating | Manufacturer |
| --- | --- | --- |
| Z-Cote HP1 | 2% dimethicone | BASF |
| Z-Cote | / | BASF |
| ZnO NDM | 5% dimethicone | H&R |
| ZnO Neutral | / | H&R |
| MZ 505 M | 5% methicone | Tayca Corp. |

Suitable titanium dioxide particles and predispersions of titanium dioxide particles are available under the following trade names from the companies listed:

| Trade name | Coating | Manufacturer |
| --- | --- | --- |
| MT-100TV | aluminum hydroxide/stearic acid | Tayca Corporation |
| MT-100Z | aluminum hydroxide/stearic acid | Tayca Corporation |
| Eusolex T-2000 | alumina/simethicone | Merck KgaA |
| Titanium dioxide T805 (Uvinul $TiO_2$) | octyltrimethylsilane | Degussa |
| Tioveil AQ 10PG | alumina/silica | Solaveil/ Uniquema |

Further advantageous pigments are latex particles. Latex particles which are advantageous according to the invention are those described in the following specifications: U.S. Pat. No. 5,663,213 and EP 0 761 201. Particularly advantageous latex particles are those which are formed from water and styrene/acrylate copolymers and are available, for example, under the trade name "Alliance SunSphere" from Rohm & Haas.

Advantageous UV-A filter substances for the purposes of the present invention are dibenzoylmethane derivatives, in particular 4-(tert-butyl)-4'-methoxydibenzoylmethane (CAS No. 70356-09-1), which is sold by Givaudan under the name Parsol® 1789 and by Merck under the trade name Eusolex® 9020.

Advantageous further UV filter substances for the purposes of the present invention are sulfonated, water-soluble UV filters, such as, for example, phenylene-1,4-bis(2-benzimidazyl)-3,3'-5,5'-tetrasulfonic acid and its salts, particularly the corresponding sodium, potassium or triethanolammonium salts, in particular the phenylene-1,4-bis(2-benzimidazyl)-3,3'-5,5'-tetrasulfonic bis-sodium salt with the INCI name Bisimidazylate (CAS No.: 180898-37-7), which is available, for example, under the trade name Neo Heliopan AP from Haarmann & Reimer;

salts of 2-phenylbenzimidazole-5-sulfonic acid, such as its sodium, potassium or its triethanolammonium salt, and the sulfonic acid itself with the INCI name Phenylbenzimidazole Sulfonic Acid (CAS No. 27503-81-7), which is available, for example, under the trade name Eusolex 232 from Merck or under Neo Heliopan Hydro from Haarmann & Reimer;

1,4-di(2-oxo-10-sulfo-3-bornylidenemethyl)benzene (also: 3,3'-(1,4-phenylene-dimethylene)bis(7,7-dimethyl-2-oxobicyclo[2.2.1]hept-1-ylmethanesulfonic acid) and salts thereof (particularly the corresponding 10-sulfato compounds, in particular the corresponding sodium, potassium or triethanolammonium salt), which is also referred to as benzene-1,4-di(2-oxo-3-bornylidenemethyl-10-sulfonic acid). Benzene-1,4-di(2-oxo-3-bornylidenemethyl-10-sulfonic acid) has the INCI name Terephtalidene Dicamphor Sulfonic Acid (CAS No.: 90457-82-2) and is available, for example, under the trade name Mexoryl SX from Chimex;

sulfonic acid derivatives of 3-benzylidenecamphor, such as e.g. 4-(2-oxo-3-bornylidenemethyl)benzenesulfonic acid, 2-methyl-5-(2-oxo-3-bornylidene-methyl)sulfonic acid and salts thereof.

Advantageous UV filter substances for the purposes of the present invention are also so-called broadband filters, i.e. filter substances which absorb both UV-A- and also UV-B-radiation.

Advantageous broadband filters or UV-B filter substances are, for example, triazine derivatives, such as e.g.

2,4-bis{[4-(2-ethylhexyloxy)-2-hydroxy]phenyl}-6-(4-methoxyphenyl)-1,3,5-triazine (INCI: Methylene Bis-Benzotriazolemethylbutylphenol), which is available under the trade name Tinosorb® S from CIBA-Chemikalien GmbH;

dioctylbutylamidotriazone (INCI: Diethylhexylbutamidotriazone), which is available under the trade name UVASORB HEB from Sigma 3V;

tris(2-ethylhexyl) 4,4',4''-(1,3,5-triazine-2,4,6-triyltriimino)trisbenzoate), also: 2,4,6-tris[anilino(p-carbo-2'-ethyl-1'-hexyloxy)]-1,3,5-triazine (INCI: Octyl Triazone), which is sold by BASF Aktiengesellschaft under the trade name UVINUL® T 150.

An advantageous broadband filter for the purposes of the present invention is also 2,2'-methylenebis(6-(2H-benzotriazol-2-yl)4-(1,1,3,3-tetramethylbutyl)phenol) (INCI: Bisoctyltriazole), which is available under the trade name Tinosorb® M from CIBA-Chemikalien GmbH.

An advantageous broadband filter for the purposes of the present invention is also 2-(2H-benzotriazol-2-yl)4-methyl-6-[2-methyl-3-[1,3,3,3-tetramethyl-1-[(trimethyl-silyl)oxy] disiloxanyl]propyl]phenol (CAS No.: 155633-54-8) with the INCI name Drometrizole Trisiloxane.

The further UV filter substances may be oil-soluble. Advantageous oil-soluble filter substances are e.g.:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)-benzoate, amyl 4-(dimethylamino) benzoate;

derivatives of benzophenone, preferably 2-hydroxy-4-methoxybenzophenone, 2-hydroxy-4-methoxy4'-methylbenzophenone, 2,2'-dihydroxy4-methoxybenzo-phenone and UV filters bound to polymers.

A further photoprotective filter substance to be used advantageously according to the invention is ethylhexyl 2-cyano-3,3-diphenyl acrylate (Octocrylene), which is available from BASF under the name Uvinul® N 539.

Particularly advantageous preparations for the purposes of the present invention, which may be characterized by a high or very high UV-A protection, comprise, as well as the filter substance(s) according to the invention, preferably also further UV-A and/or broadband filters, in particular dibenzoylmethane derivatives [for example 4-(tert-butyl)-4'-methoxydibenzoylmethane] and/or 2,4-bis{[4-(2-ethylhexyloxy)-2-hydroxy]phenyl}-6-(4-methoxyphenyl)-1,3,5-triazine, in each case individually or in any combinations with one another.

The list of UV filters specified which can be used for the purposes of the present invention is not of course intended to be limiting.

Advantageously, the preparations according to the invention comprise the substances which absorb UV radiation in the UV-A and/or UV-B region in a total amount of e.g. 0.1% by weight to 30% by weight, preferably 0.5 to 20% by weight, in particular 1.0 to 15.0% by weight, in each case based on the total weight of the preparations, in order to provide cosmetic preparations which protect the hair and/or the skin from the entire range of ultraviolet radiation.

In addition, it may in some instances be advantageous to incorporate film formers into the cosmetic or dermatological preparations according to the invention, for example in order to improve the water resistance of the preparations or to increase the UV protection performance (UV-A and/or UV-B boosting). Water-soluble or dispersible and also fat-soluble film formers are suitable, in each case individually or in combination with one another.

Advantageus water-soluble or dispersible film formers are e.g. polyurethanes (e.g the Avalure® grades from Goodrich), dimethicone copolyol polyacrylate (Silsoft Surface® from Witco Organo Silicones Group), PVP/VA (VA=vinyl acetate) copolymer (Luviscol VA 64 Powder from BASF) etc.

Advantageous fat-soluble film formers are e.g. the film formers from the group of polymers based on polyvinylpyrrolidone (PVP)

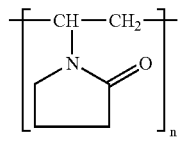

Particular preference is given to copolymers of polyvinylpyrrolidone, for example the PVP hexadecene copolymer and the PVP eicosene copolymer, which are available under the trade names Antaron V216 and Antaron V220 from GAF Chemicals Cooperation and also tricontayl PVP and the like.

The examples below serve to illustrate the present invention without limiting it. The numerical values in the examples are percentages by weight, based on the total weight of the particular preparations.

EXAMPLES

1. O/W Sunscreen Emulsions

|  | 1 | 2 | 3 | 4 | 5 | 6 | 7 |
|---|---|---|---|---|---|---|---|
| Glycerol monostearate SE | 0.50 | 1.00 | 3.00 |  |  | 1.50 |  |
| Glyceryl stearate citrate | 2.00 |  |  | 1.00 | 1.00 |  | 2.50 |
| Stearic acid |  | 3.00 |  | 2.00 |  |  |  |
| PEG-40 stearate | 0.50 |  |  |  |  | 2.00 |  |
| PEG-100 stearate |  | 1.50 |  |  | 3.00 |  |  |
| Cetyl phosphate |  |  |  |  | 1.00 |  |  |
| Stearyl alcohol |  |  | 3.00 |  |  | 2.00 | 0.50 |
| Cetyl alcohol | 2.50 | 1.00 |  | 1.50 | 0.50 |  | 2.00 |
| Ethylhexyl methoxycinnamate |  |  |  | 5.00 | 6.00 |  | 8.00 |
| Anisotriazine |  | 1.50 |  | 2.00 | 2.50 |  | 2.50 |
| Butylmethoxydibenzoylmethane | 3.00 | 3.00 | 2.00 |  |  |  | 1.50 |
| Bisimidazylate |  |  | 0.50 |  | 1.00 |  | 0.30 |
| Ethylhexyltriazone | 4.00 |  | 3.00 |  | 4.00 |  |  |
| 4-Methylbenzylidenecamphor |  |  |  |  |  |  | 2.00 |
| Octocrylene | 10.0 | 4.00 |  |  |  |  | 2.50 |
| Diethylhexylbutamidotriazone | 1.00 |  |  | 2.00 | 1.00 |  |  |
| Phenylbenzmidazolesulfonic acid | 0.50 |  |  | 3.00 |  |  |  |
| Bisoctyltriazole | 2.00 |  | 0.50 | 1.50 | 2.50 |  |  |
| Benzophenone-3 |  |  |  | 5.50 |  |  |  |
| Homosalate |  | 2.00 |  |  |  |  |  |
| Ethylhexylsalicylate |  |  | 3.00 |  |  |  | 5.00 |
| Drometrizole trisiloxane |  |  | 0.5 |  |  |  |  |
| Terephthalidenedicamphor-sulfonic acid |  | 1.50 |  |  | 1.00 |  |  |
| Diethylhexyl-2,6-naphthalate | 10.0 | 4.80 | 7.00 | 9.50 | 6.70 | 5.50 | 8.00 |
| Titanium dioxide MT-100Z | 1.00 |  |  | 3.00 |  |  |  |
| Z-Cote HP1 |  |  | 1.50 | 1.00 |  |  | 3.00 |
| C12–15 alkylbenzoate |  | 2.50 |  |  | 4.00 | 7.00 | 5.00 |
| Dicaprylyl ether |  |  | 3.50 |  | 2.00 |  |  |
| Butylene glycol dicaprylate/Dicaprate | 5.00 |  |  | 6.00 |  |  |  |
| Dicaprylyl carbonate |  |  | 6.00 |  |  | 2.00 | 2.00 |
| Dimethicone |  | 0.50 | 1.00 |  | 2.00 |  |  |
| Dibutyl adipate |  |  |  | 3.00 |  |  |  |
| Coco-caprylate/caprate |  | 4.50 |  |  | 5.00 |  |  |
| Cyclomethicone | 2.00 |  |  | 0.50 | 3.00 |  | 0.50 |
| Shea butter |  | 2.00 |  |  |  |  | 0.50 |
| PVP hexadecene copolymer | 0.50 |  |  | 0.50 | 1.00 |  | 1.00 |
| Tricontanyl PVP |  | 0.50 | 1.00 |  |  |  | 1.00 |
| Glycerol | 3.00 | 7.50 |  | 7.50 | 5.00 |  | 2.50 |
| Xanthan gum | 0.15 |  | 0.05 |  |  |  | 0.30 |
| Sodium carbomer |  | 0.20 | 0.10 | 0.20 |  |  |  |
| Vitamin E | 0.50 |  | 0.25 |  | 0.75 |  | 1.00 |
| Vitamin A |  | 0.15 |  |  |  |  |  |
| Fucogel ® 1000 |  |  |  | 1.50 | 3.00 |  |  |
| Polyurethane |  |  |  | 0.50 |  |  |  |
| Styrene/acrylate copolymer | 0.80 |  |  | 0.20 |  |  |  |
| DMDM hydantoin |  | 0.60 | 0.40 | 0.20 |  |  |  |
| Konkaben LMB ® |  |  |  | 0.18 | 0.20 |  | 0.15 |
| EDTA | 0.20 |  | 0.75 |  | 0.35 | 0.15 |  |
| Methylparaben | 0.15 |  | 0.25 |  | 0.50 |  |  |
| Phenoxyethanol | 1.00 | 0.40 |  | 0.40 | 0.50 | 0.40 | 0.60 |
| Ethanol |  | 2.00 | 1.50 |  | 3.00 |  | 1.00 |
| Perfume | 0.20 |  | 0.20 |  | 0.20 | 0.20 | 0.20 |
| Water | ad 100 | ad 100 | ad 100 | Ad 100 | ad 100 | ad 100 | ad 100 |

2. Hydrodispersions

| | 1 | 2 | 3 | 4 | 5 |
|---|---|---|---|---|---|
| Ceteareth-20 | 1.00 | | | | |
| Cetyl alcohol | | | 1.00 | | |
| Sodium carbomer | | 0.20 | | 0.30 | |
| Acrylates/C10–30 alkyl acrylate crosspolymer | 0.50 | | 0.40 | 0.10 | 0.10 |
| Xanthan gum | | 0.30 | 0.15 | | 0.50 |
| Aristoflex ® AVC | 0.50 | | | | |
| Ethylhexyl methoxycinnamate | | | | 5.00 | 8.00 |
| Anisotriazine | | 1.50 | | 2.00 | 2.50 |
| Butylmethoxydibenzoylmethane | 1.00 | 0.50 | | 3.00 | |
| Bisimidazylate | | 1.80 | | 2.00 | 3.00 |
| Ethylhexyltriazone | 4.00 | | 3.00 | 4.00 | |
| 4-Methylbenzylidenecamphor | 4.00 | | | | |
| Octocrylene | | 4.00 | 3.90 | | 2.50 |
| Diethyhexylbutamidotriazone | 1.00 | | | 2.00 | |
| Phenylbenzimidazolesulfonic acid | 0.50 | | | 3.00 | |
| Bisoctyltriazole | 2.50 | 0.50 | | | 0.80 |
| Drometrizole trisiloxane | | | 1.00 | | 1.50 |
| Terephthalidenedicamphor-sulfonic acid | | 0.50 | | | 1.00 |
| Diethylhexyl 2,6-naphthalate | 4.50 | 8.00 | 7.20 | 5.50 | 15.00 |
| Titanium dioxide MT-100TV | 0.50 | | 2.00 | | 1.00 |
| Zinc oxide NDM | | | 1.00 | | |
| C12–15 alkyl benzoate | 2.00 | 2.50 | | | |
| Octyldodecanol | | 4.00 | 5.00 | | |
| Butylene glycol dicaprylate/dicaprate | 4.00 | | 2.00 | 6.00 | |
| Dicaprylyl carbonate | | 2.00 | 6.00 | | |
| Isohexadecene | 3.00 | | | | |
| Dimethicone | | | 0.50 | 1.00 | |
| Phenyltrimethicone | 2.00 | | | 0.50 | 2.00 |
| Shea butter | | 2.00 | | | |
| PVP hexadecene copolymer | 0.50 | | | 0.50 | 1.00 |
| Tricontanyl PVP | 0.50 | | 1.00 | | |
| Ethylhexylglycerol | | | 1.00 | | 0.50 |
| Glycerol | 3.00 | 7.50 | | 7.50 | 2.50 |
| Glycine soya | | | 1.50 | | |
| Vitamin E | 0.50 | | 0.25 | | 1.00 |
| Vitamin F | | 0.50 | | | |
| α-Glucosylrutin | | | 0.20 | | |
| Polyurethane | | 0.60 | 1.50 | 1.00 | |
| Styrene/acrylate copolymer | | 2.50 | 0.50 | | |
| DMDM hydantoin | | 0.60 | 0.40 | 0.20 | |
| Konkaben LMB ® | 0.20 | | | | |
| Octoxyglycerol | | 0.25 | | 0.50 | 1.00 |
| EDTA | 0.15 | 0.05 | | | |
| Glycine soya | | | | 0.50 | 1.50 |
| Methylparaben | 0.50 | | 0.25 | 0.15 | |
| Phenoxyethanol | 0.50 | 0.40 | | 1.00 | |
| Ethanol | 3.00 | 2.00 | 1.50 | | 7.00 |
| Perfume | 0.20 | 0.20 | 0.20 | | |
| Water | ad 100 | ad 100 | ad 100 | ad 100 | ad 100 |

3. W/O Sunscreen Emulsions

| | 1 | 2 | 3 | 4 | 5 |
|---|---|---|---|---|---|
| Cetyldimethicone copolyol | | 2.50 | | 4.00 | |
| Polyglyceryl-2 dipolyhydroxystearate | 5.00 | 2.50 | | | 4.50 |
| PEG-30 dipolyhydroxystearate | | | 5.00 | | |
| Laurylmethicone copolyol | | | 2.00 | | |
| Ethylhexyl methoxycinnamate | | 8.00 | | 5.00 | |
| Anisotriazine | | 2.50 | | 2.00 | |
| Butylmethoxydibenzoylmethane | 3.00 | 2.00 | 1.00 | | |
| Bisimidazylate | | | | 2.00 | 2.60 |
| Ethylhexyltriazone | | | 3.00 | 4.00 | |
| 4-Methylbenzylidenecamphor | | 2.00 | 4.00 | 2.00 | |
| Octocrylene | | 2.50 | 3.90 | | 10.0 |
| Diethyhexylbutamidotriazone | | | | 2.00 | |
| Phenylbenzimidazolesulfonic acid | | | 0.50 | 3.00 | |
| Bisoctyltriazole | | | 2.00 | 0.50 | |
| Drometrizole trisiloxane | | 1.00 | | | 1.50 |
| Terephthalidenedicamphor-sulfonic acid | | | 1.00 | | 0.50 |
| Diethylhexyl 2,6-naphthalate | 7.50 | 5.50 | 3.50 | 8.80 | 9.70 |
| Titanium dioxide T805 | | 2.00 | 1.50 | | 3.00 |
| Z-Cote ® HP1 | | | | | 7.00 |
| Mineral oil | | | 10.0 | | 8.00 |
| C12–15 alkyl benzoate | | | | 9.00 | |
| Dicaprylyl ether | 10.00 | | | | 7.00 |
| Butylene glycol dicaprylate/dicaprate | | | 2.00 | 8.00 | 4.00 |
| Dicaprylyl carbonate | 5.00 | | 6.00 | | |
| Cocoglycerides | | 3.00 | | | 5.50 |
| Dibutyl adipate | | | | 4.50 | |
| Dimethicone | | | 4.00 | 1.00 | 5.00 |
| Cyclomethicone | 2.00 | 25.00 | | | 2.00 |
| Shea butter | | | 3.00 | | |
| PVP hexadecene copolymer | 0.50 | | | 0.50 | 1.00 |
| Tricontanyl PVP | | | 0.50 | 1.00 | 0.50 |
| Ethylhexylglycerol | | 0.30 | 1.00 | | 0.50 |
| Glycerol | 3.00 | 7.50 | | 7.50 | 2.50 |
| Glycine soya | | 1.00 | 1.50 | | |
| MgSO$_4$ | 1.00 | 0.50 | | 0.50 | |
| MgCl$_2$ | | | 1.00 | | 0.70 |
| Vitamin E acetate | 0.50 | | | 0.25 | 1.00 |
| Ubiquinone Q 10 | 0.25 | 0.10 | | | |
| Panthenol | | | 0.50 | | |
| Iminodisuccinic acid | 0.30 | | | 0.50 | |
| DMDM hydantoin | | 0.60 | | 0.40 | 0.20 |
| Methylparaben | 0.50 | | | 0.25 | 0.15 |
| Phenoxyethanol | 0.50 | 0.40 | | 1.00 | 0.60 |
| Ethanol | 3.00 | | 1.50 | | 1.00 |
| Perfume | 0.20 | | 0.20 | | 0.20 |
| Water | ad 100 | ad 100 | ad 100 | ad 100 | ad 100 |

4. Solids-stabilized Emulsions

| | 1 | 2 | 3 | 4 | 5 |
|---|---|---|---|---|---|
| Mineral oil | | | | 16.0 | 16.0 |
| Octyldodecanol | 9.0 | 9.0 | 5.0 | | |
| Caprylic/capric triglyceride | 9.0 | 9.0 | 6.0 | | |
| C12–15-alkyl benzoate | | | | 5.0 | 8.0 |
| Butylene glycol dicaprylate/dicaprate | | | | | 8.0 |
| Dicaprylyl ether | 9.0 | | | 4.0 | |
| Dicaprylyl carbonate | | 9.0 | | | |
| Hydroxyoctacosanyl hydroxystearate | 2.0 | 2.0 | 2.0 | 2.0 | 1.5 |
| Disteardimonium hectorite | 1.0 | 0.75 | 0.5 | 0.5 | 0.25 |
| Cera microcristallina + Paraffinum liquidum | | | | | 5.0 |
| Hydroxypropylmethylcellulose | | | | | 0.05 |
| Dimethicone | | | | | 3.0 |
| Butylmethoxydibenzoylmethane | | 0.50 | 3.50 | | 0.50 |
| Ethylhexyl methoxycinnamate | 10.0 | | | | 3.0 |
| 4-Methylbenzylidenecamphor | | | | | 4.0 |
| Diethylhexylbutamidotriazone | | | | | 4.0 |
| Anisotriazine | 0.50 | | | 2.0 | |
| Drometrizol trisiloxane | | 0.50 | | 1.0 | |
| Terephthalidenedicamphor-sulfonic acid | | 1.00 | 0.50 | | 1.50 |
| Bisimidazylate | 2.50 | | | 1.50 | 0.50 |
| Eusolex ® T-2000 | | 2.0 | 4.0 | 2.0 | 4.0 |
| Uvinul ® T805 | | | | | 3.00 |
| Zinc oxide HP1 | 1.50 | | | 6.0 | |
| Silica dimethyl silylate | | | 1.0 | | 0.5 |

-continued

|  | 1 | 2 | 3 | 4 | 5 |
|---|---|---|---|---|---|
| Boron nitride | 2.0 | | | | |
| Starch/sodium metaphosphate polymer | | 0.5 | | | |
| Diethylhexyl 2,6-naphthalate | 5.00 | 7.00 | 8.50 | 3.00 | 4.50 |
| Tapioca starch | | | | 1.0 | |
| Sodium chloride | 1.0 | 1.0 | 1.0 | 1.0 | 1.0 |
| Glycerol | 5.0 | 10.0 | 3.0 | 6.0 | 10.0 |
| Trisodium EDTA | | 1.0 | | 1.0 | |
| Methylparaben | 0.21 | | | | 0.2 |
| Propylparaben | 0.07 | | | | |
| Phenoxyethanol | 0.5 | | 0.4 | 0.4 | 0.5 |
| Hexamidine diisethionate | | | | | 0.08 |
| Diazolidinylurea | | | 0.28 | 0.28 | |
| Alcohol | | | | 2.5 | |
| Perfume | q.s. | q.s. | q.s. | q.s. | q.s. |
| Water | ad 100 | ad 100 | ad 100 | ad 100 | ad 100 |

5. PIT Emulsions

|  | 1 | 2 | 3 | 4 | 5 | 6 | 7 | 8 |
|---|---|---|---|---|---|---|---|---|
| Glycerol monostearate SE | 0.50 | 2.00 | 3.00 | 5.00 | | | 0.50 | 4.00 |
| Glyceryl isostearate | | | | | 3.50 | 4.00 | 2.00 | |
| Isoceteth-20 | | 0.50 | | | 2.00 | | | |
| Ceteareth-12 | | 5.00 | | 1.00 | | | | 3.50 |
| Ceteareth-20 | | | | 2.00 | | 2.50 | 3.00 | |
| PEG-100 stearate | 5.00 | | 1.00 | | 1.00 | | | 0.50 |
| Cetyl alcohol | 2.50 | 1.00 | | 1.50 | | 0.50 | 1.50 | |
| Cetyl palmitate | | | | 0.50 | | 1.00 | | |
| Cetyl Dimethicone copolyol | 0.50 | | | | 0.50 | | 1.00 | |
| Polyglyceryl-2 dipolyhydroxystearate | | | | 0.75 | 0.25 | | | |
| Diethylhexyl 2,6-naphthalate | 7.0 | 3.5 | 1.0 | 6.0 | 0.5 | 4.0 | 5.0 | 4.5 |
| Anisotriazine | | | 0.50 | 2.00 | | 3.00 | | |
| Butylmethoxydibenzoylmethane | 1.50 | | 1.00 | | | | | |
| Bisimidazylate | | 2.00 | | | | | | |
| Terephthalidenedicamphor-sulfonic acid | | | 0.50 | | | | 1.00 | |
| Drometrizole trisiloxane | | 2.00 | | | | 3.00 | | 1.00 |
| Ethylhexyl methoxycinnamate | 8.00 | | | 4.50 | | 8.00 | | |
| Ethylhexyl salicylate | 4.00 | | | | | 4.00 | | |
| Dioctylbutamidotriazone | | | | 3.00 | | 2.00 | | 1.50 |
| Ethylhexyltriazone | | | 2.00 | 4.00 | | | 1.50 | 3.00 |
| Dimethicone diethylbenzalmalonate | | 4.50 | | | | | | |
| Octocrylene | | | | 5.00 | | | | 7.50 |
| Phenylbenzmidazolesulfonic acid | 1.00 | 5.00 | | 3.00 | | | | |
| C12–15 alkylbenzoate | 3.50 | | | | 6.50 | 4.00 | | |
| Cocoglycerides | | 3.00 | | 3.00 | | 2.50 | | 3.50 |
| Dicaprylyl ether | 4.00 | | | | | | | |
| Butylene glycol dicaprylate/dicaprate | | 4.00 | | 3.00 | | | | |
| Dicaprylyl carbonate | | | | 0.50 | | | | 6.00 |
| Dibutyl adipate | | | 2.50 | | | 3.00 | | 1.00 |
| Phenyltrimethicone | 2.00 | | | | | 3.00 | | |
| Cyclomethicone | | 3.00 | | | | | | 4.00 |
| PVP hexadecene copolymer | | | | 1.00 | 1.50 | | | |
| Glycerol | 10.0 | 5.00 | | 7.50 | | | | |
| Tocopherol | 1.00 | | | 0.75 | 0.50 | | 1.00 | |
| Shea butter | | 2.00 | | | | | | 0.50 |
| Iodopropyl butylcarbamate | 0.12 | | | | 0.20 | 0.15 | | |
| DMDM hydantoin | | | | 0.10 | | | | |
| Methylparaben | | 0.50 | 0.25 | | 0.45 | | | |
| Phenoxyethanol | 0.50 | 0.40 | | 1.00 | | | | 1.00 |
| Octoxyglycerol | | 0.30 | | | 1.00 | | | |
| Ethanol | | | | 2.00 | | | 7.50 | 4.00 |
| Trisodium EDTA | | 0.40 | | 0.15 | | 0.20 | | 0.50 |
| Perfume | 0.20 | | 0.20 | 0.20 | 0.45 | | | 0.20 |
| Water | ad 100 | ad 100 | ad 100 | ad 100 | ad 100 | ad 100 | ad 100 | ad 100 |

That which is claimed:

1. A cosmetic or dermatological formulation, comprising:
   (a) at least one oxidation- and/or UV-sensitive active ingredient;
   (b) at least one dialkyl naphthalate which is distinguished by the structural formula

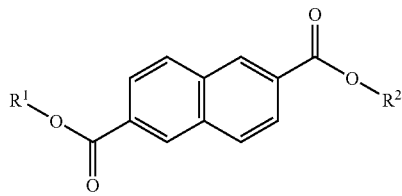

in which where $R^1$ and $R^2$, independently of one another, are chosen from the group of branched and unbranched alkyl groups having 6 to 24 carbon atoms, and (c) at least one lipid with a polarity of at most 30 mN/m, the at least one lipid is present in an amount from 0.0001 to 10% by weight, based on the total weight of the formulation.

2. The formulation as claimed in claim 1, wherein the at least one dialkyl naphthalate is present in an amount from 0.001 to 30% by weight, based on the total weight of the formulation.

3. The formulation as claimed in claim 1, wherein the at least one dialkyl naphthalate is present in an amount from 0.01 to 20% by weight, based on the total weight of the formulation.

4. The formulation as claimed in claim 1, wherein the at least one dialkyl naphthalate is present in an amount from 1 to 15% by weight, based on the total weight of the formulation.

5. The formulation as claimed in claim 1, wherein at least one of $R^1$ and $R^2$ is a branched alkyl group having 6 to 10 carbon atoms.

6. The formulation as claimed in claim 1, wherein $R^1$ and $R^2$ are branched alkyl groups having 6 to 10 carbon atoms.

7. The formulation as claimed in claim 1, wherein the at least one dialkyl naphthalate includes diethylhexyl naphthalate.

8. The formulation as claimed in claim 1, wherein the at least one oxidation-sensitive or UV-sensitive active ingredient includes 4-(tert-butyl)-4'-methoxydibenzoyl-methane.

9. The formulation as claimed in claim 1, wherein the at least one oxidation-sensitive or UV-sensitive active ingredient includes at least one lipophilic active ingredient.

10. The formulation as claimed in claim 1, wherein the at least one oxidation-sensitive or UV-sensitive active ingredient is selected from the group consisting of coenzyme Q10, vitamin A and derivatives thereof, vitamin E and derivatives thereof, lipophilic acid and derivatives thereof, and carotinoids.

11. The formulation as claimed in claim 1, further comprising at least one UV filter substance selected from the group consisting of triazines, benzotriazoles, organic pigments and inorganic pigments.

12. The formulation as claimed in claim 1, further comprising at least one UV-A filter substance or broadband filter selected from the group consisting of 2,4-bis{[4-(2-ethyl-hexyloxy)-2-hydroxy]phenyl}-6-(4-methoxy- phenyl)-1,3,5-triazine, phenylene-1,4-bis(2-benzimidazyl)-3,3'-5,5'-tetras- ulfonic acid bis-sodium salt, and mixtures thereof.

13. The formulation as claimed in claim 1, wherein the at least one lipid with a polarity of at most 30 mN/m includes at least one lipid with at least one lipid with a polarity of 5 mN/m to 25 mN/m.

14. The formulation as claimed in claim 1, wherein the at least one lipid is selected from the group consisting of olive oil, sunflower oil, soybean oil, groundnut oil, rapeseed oil, almond oil, palm oil, coconut oil, castor oil, wheatgerm oil, grapeseed oil, thistle oil, evening primrose oil, macadamia nut oil, corn oil and avocado oil.

15. The formulation as claimed in claim 1, wherein the at least one lipid is selected from the group consisting of isodecyl neopentanoate, isohexyl decanoate, isodecyl octanoate, dihexyl ether, isodecyl 3,5,5-trimethyl hexanoate, cetearyl isononanoate, isopropyl palmitate, cyclomethicone, cyclopolydimethylsiloxane, jojoba oil gold, dimethicone, 2-ethylhexanoic acid 3,5,5-trimethyl ester, often, octyldode-canol, hexyl decanol, isotridecyl 3,5,5-trimethylhex- anonanoate, hexyldecanol, hexyl decyl laurate, octyl palmitate, octyldodecyl myristate, macadamia nut oil, phenyl trimethicone, butyl octanoic acid, isopropyl stearate, C12–15 alkyl benzoate, butylene glycol caprylate/caprate, caprylic/capric triglyceride, tricaprylin, PEG diethyl hex- anoate/diisononanoate/ethylhexy- l isononanoate, butyl decanol, hexyl octanol, butyl octanol, tridecyl stearate, tride- cyl trimellitate, dipentaerythrityl hexacaprylate/hexacaprate, castor oil, propylene glycol dicaprylate/dicaprate, butyl octanol, stearyl heptanoate, avocado oil, dibutyl adipate, PEG 2 diethylene hexanoate, C12–13 alkyl lactate, diethyl- ene glycol dioctanoate/diisononanoate, di-C12–13 alkyl tar- trate, propylene glycol monoisostearate, cocoglycerides and triisostearin.

16. The formulation as claimed in claim 1, wherein the at least one lipid is selected from the group consisting of paraffin oil, hydrogenated polyisobutenes, squalane and squalene.

17. The formulation as claimed in claim 1, wherein the at least one lipid is selected from the group consisting of UV filter substances which are liquid at room temperature.

18. The formulation as claimed in claim 17, wherein the UV filter substances which are liquid at room temperature are selected from the group consisting of homomenthyl salicylate, 2-ethylhexyl 2-cyano-3,3-diphenylacrylate, 2-ethylhexyl 2-hydroxybenzoate, 4-methoxycinnamic 2-ethyihexyl ester and 4-methoxycinnamic isopentyl ester.

19. The formulation as claimed in claim 1, further comprising at least one lipid having a polarity of greater than or equal to 30 mN/m.

20. The formulation as claimed in claim 1, further comprising at least one oil or wax selected from the group consisting of cyclic and linear silicone oils, and silicone waxes.

21. A method for moisturizing skin, comprising applying to the skin a cosmetic or dermatological formulation, comprising:
(a) at least one oxidation-sensitive or UV-sensitive active ingredient;
(b) at least one dialkyl naphthalate which is distinguished by the structural formula

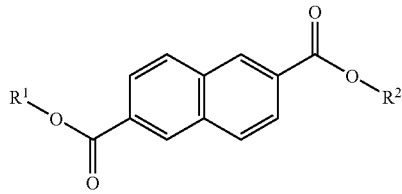

in which where $R^1$ and $R^2$, independently of one another, are chosen from the group of branched and unbranched alkyl groups having 6 to 24 carbon atoms, and
(c) at least one lipid with a polarity of at most 30 mN/m, the at least one lipid is present in an amount from 0.0001 to 10% by weight, based on the total weight of the formulation.

22. A method for protecting the skin against photoinduced skin aging, comprising applying to the skin a cosmetic or dermatological formulation, comprising:
(a) at least one oxidation-sensitive or UV-sensitive active ingredient;

(b) at least one dialkyl naphthalate which is distinguished by the structural formula

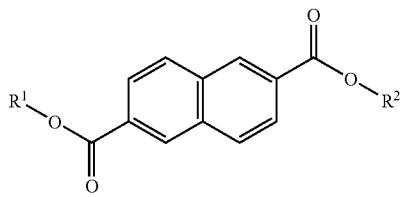

in which where $R^1$ and $R^2$, independently of one another, are chosen from the group of branched and unbranched alkyl groups having 6 to 24 carbon atoms, and (c) at least one lipid with a polarity of at most 30 mN/m, the at least one lipid is present in an amount from 0.0001 to 10% by weight, based on the total weight of the formulation.

23. A method for stabilizing cosmetic or dermatological active ingredients against decomposition induced by UV radiation, comprising adding to an active ingredient-containing cosmetic or dermatological formulation (a) at least one dialkyl naphthalate which is distinguished by the structural formula

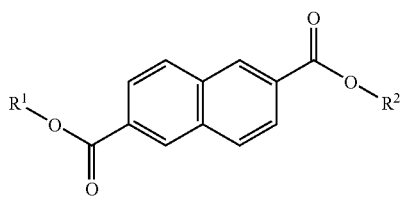

in which where $R^1$ and $R^2$, independently of one another, are chosen from the group of branched and unbranched alkyl groups having 6 to 24 carbon atoms, and (b) at least one lipid with a polarity of at most 30 mN/m, the at least one lipid is present in an amount from 0.0001 to 10% by weight, based on the total weight of the formulation.

24. A method for improving the effectiveness and increasing the stability of lipophilic active ingredients in cosmetic or dermatological preparations, comprising adding to an lipophilic active ingredient-containing cosmetic or dermatological formulation (a) at least one dialkyl naphthalate which is distinguished by the structural formula

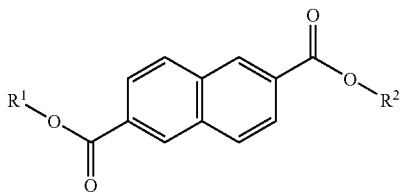

in which where $R^1$ and $R^2$, independently of one another, are chosen from the group of branched and unbranched alkyl groups having 6 to 24 carbon atoms, and (b) at least one lipid with a polarity of at most 30 mN/m, the at least one lipid is present in an amount from 0.0001 to 10% by weight, based on the total weight of the formulation.

25. The formulation as claimed in claim 1, wherein the at least one lipid is present in an amount from 0.001 to 5% by weight, based on the total weight of the formulation.

* * * * *